United States Patent [19]
Hernandez-Guerra et al.

[11] Patent Number: 6,118,847
[45] Date of Patent: *Sep. 12, 2000

[54] SYSTEM AND METHOD FOR GATED RADIOTHERAPY BASED ON PHYSIOLOGICAL INPUTS

[75] Inventors: Francisco M. Hernandez-Guerra, Concord; Edward Lewis Calderon, Pittsburg; Hussein Alrifai, Pleasant Hill; David L. Pond, Novato; Simon John Forknall, Concord; Pat Merola, Walnut Creek, all of Calif.

[73] Assignee: Siemens Medical Systems, Inc., Iselin, N.J.

[ * ] Notice: This patent is subject to a terminal disclaimer.

[21] Appl. No.: 09/130,303

[22] Filed: Aug. 6, 1998

Related U.S. Application Data

[63] Continuation-in-part of application No. 09/007,441, Jan. 15, 1998, Pat. No. 6,052,435.
[60] Provisional application No. 60/075,990, Feb. 25, 1998.

[51] Int. Cl.[7] ........................................ A61N 5/10
[52] U.S. Cl. ...................... 378/65; 378/108; 250/505.1
[58] Field of Search ............................... 378/65, 105, 108, 378/195, 119, 95; 250/492.1, 492.3, 505.1

[56] References Cited

U.S. PATENT DOCUMENTS

| | | | |
|---|---|---|---|
| 5,148,032 | 9/1992 | Hernandez | 378/151 |
| 5,155,752 | 10/1992 | Kawakami | 378/97 |
| 5,332,908 | 7/1994 | Weidlich | 378/65 |
| 5,538,494 | 7/1996 | Matsuda | 378/65 |
| 5,563,925 | 10/1996 | Hernandez | 378/65 |

OTHER PUBLICATIONS

Hideo D. Kubo and Bruce C. Hill, "Respiration Gated Radiotherapy Treatment: A Technical Study," Phys. Med. Biol., vol. 41 pp. 83–91 (1996).

*Primary Examiner*—David P. Porta
*Assistant Examiner*—Drew A. Dunn

[57] ABSTRACT

A radiation therapy device (2) configured to receive a signal indicative of one or more of a patient's physiological parameters. The signal controls a gating, whereby a phase of an RF pulse (1002) and an injector pulse (1006) are varied so as to inhibit X-ray production without affecting injector or RF amplitudes.

19 Claims, 12 Drawing Sheets

SYSTEM AND METHOD FOR GATED RADIOTHERAPY BASED ON PHYSIOLOGICAL INPUTS

CROSS REFERENCE TO RELATED APPLICATIONS

This application is a continuation-in-part of application Ser. No. 09/007,441, titled "Precision Beam Control for an Intensity Modulation Treatment System," filed Jan. 15, 1998 now U.S. Pat. No. 6,052,435 (Our File 98 P 7404 US), and also claims priority of provisional application Ser. No. 60/075,990, filed Feb. 25, 1998, titled "Design & Clinical Implementation of a System for Respiratory Gated Radiotherapy" (Our File 98 P 7427 US). This case is related to applications Ser. No. 09/007,304, entitled "Precision Dosimetry in an Intensity Modulated Radiation Treatment System" (Our File: 98 P 7403 US) and Ser. No. 09/007,444, entitled "System and Method for Dose Monitoring in an Intensity Modulated Radiation Treatment System," both filed Jan. 15, 1998 (Our File 98 P 7405 US).

BACKGROUND OF THE INVENTION

The present invention relates to radiation therapy, and more particularly, to a system and method for efficiently delivering radiation treatment.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

In the case of an electron beam, for example, the electron accelerator typically includes an electron gun, accelerating cavities, an exit window, and a radio frequency input. A trigger system generates modulator and injector signals and supplies them to an injector and a high voltage modulator. The modulator generates the radio frequency pulses and the injector generates the injector pulses. The injector pulses control the quantity of the electrons that will be emitted by the electron gun. The radio frequency creates an electromagnetic field in the accelerator which accelerates the electron beam toward the exit window. The injector and the radio frequency pulses must be synchronized; otherwise, beam acceleration will not occur.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

An exemplary target volume is illustrated in FIG. 1. The gross tumor volume (GTV) and clinical target volume (CTV) contain tissues to be treated. The planning target volume (PTV) places a margin around the CTV to account for patient movement and uncertainties in patient setup. The planning target volume (PTV) is defined to select appropriate beam sizes and beam arrangements taking into consideration the net affect of all the possible geometric variations in order to ensure that the prescribed dose is actually absorbed in the CTV. The treated volume is the volume enclosed by an isodose surface selected and specified by the radiation oncologist as being appropriate to achieve the purpose of treatment.

The ultimate goal of radiation therapy is to deliver a treatment in which the CTV, PTV and treated volumes are identical. A difficulty in achieving this goal may arise because of voluntary and involuntary patient movement.

Accordingly, it is desirable to predict when the patient will move and adjust radiation delivery accordingly. Various physiological parameters and indicia are relevant to movement, and may be used to gauge when a patient is about to move. Such parameters include, for example, muscle contraction, alpha (brain) waves, blinking, cardiac movement, respiration, and the like.

For example, in the thorax and abdomen, the PTV margin beyond the CTV is relatively large. A large contributory factor is the organ motion due to respiration. In diagnostic imaging, organ motion has been recognized as a significant cause of image blurring. Several techniques have been used in diagnostic imaging to reduce respiratory organ motion. Retrospective or prospective image correction techniques such as navigator echo imaging work well for MRI (magnetic resonance imaging), but are not applicable to radiation therapy. Breath holding has been used with success for spiral CT (Computed Tomography) scanner image acquisition but is not practical for radiation therapy because the beam on time is typically too long for most patients to their breaths.

In addition, in radiation therapy, the challenge is not simply to freeze respiratory motion for a single session, as in the case of diagnostic imaging, but to do so reproducing patient position between consecutive respiratory cycles, radiation beams and treatment days. The procedure employed must ensure reproducibility of organ position not only during treatment but for diagnostic image acquisition used in treatment planning as well.

SUMMARY OF THE INVENTION

These problems and the prior art are overcome in large part by a system and method for control of radiation therapy delivery according to the present invention.

According to one embodiment, a physiology monitor may be used to characterize a patient's physiological mechanics by means of a sensor. The signal from the physiological monitor is used to generate a gating signal to gate the radiation beam at the optimal periods. Treatment commences with the accelerator fully powered up but with x-ray production inhibited by injecting electrons into the accelerator wave guide out of phase. When the gating signal from the respiratory monitor is received, the electrons are injected at the proper time and beam on commences. The electron injection is phase shifted in and out without affecting either the injector or the RF pulse amplitudes, thereby allowing fast transitions between no beam and beam on in conjunction with the physiological monitor.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

SYSTEM OVERVIEW

Figure 1:
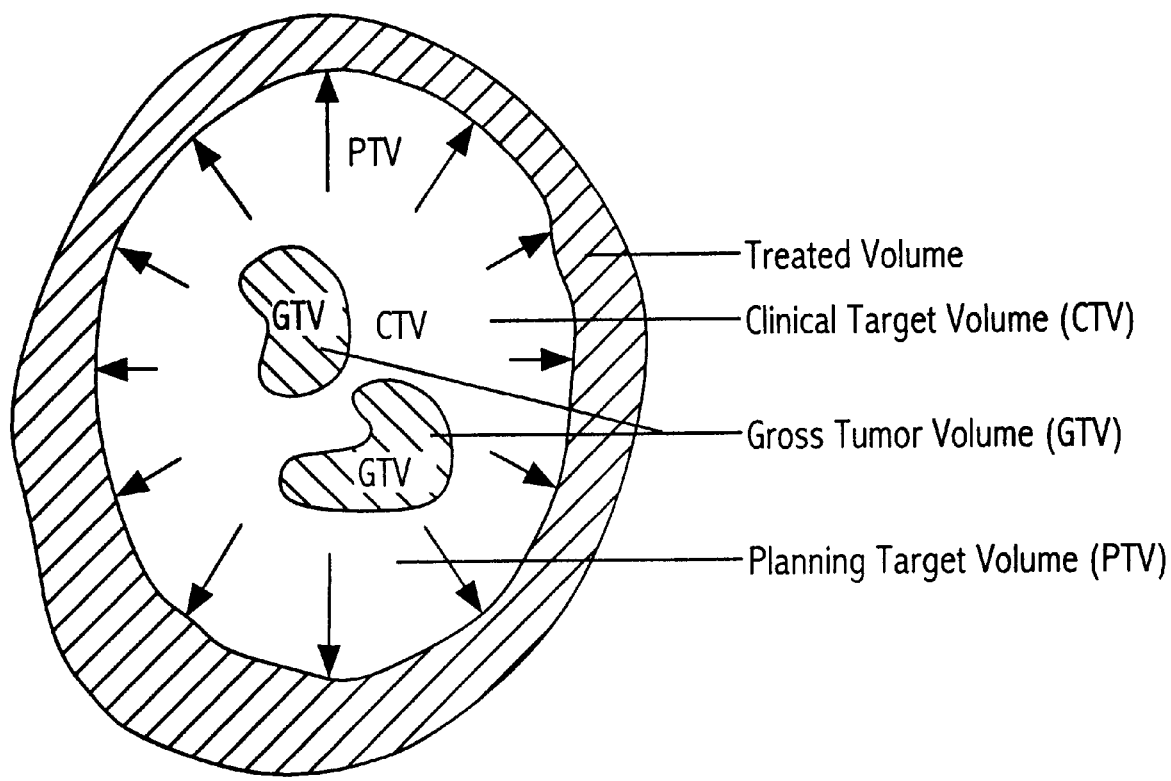
FIG. 1 is a diagram of an exemplary treatment volume.
Figure 2:
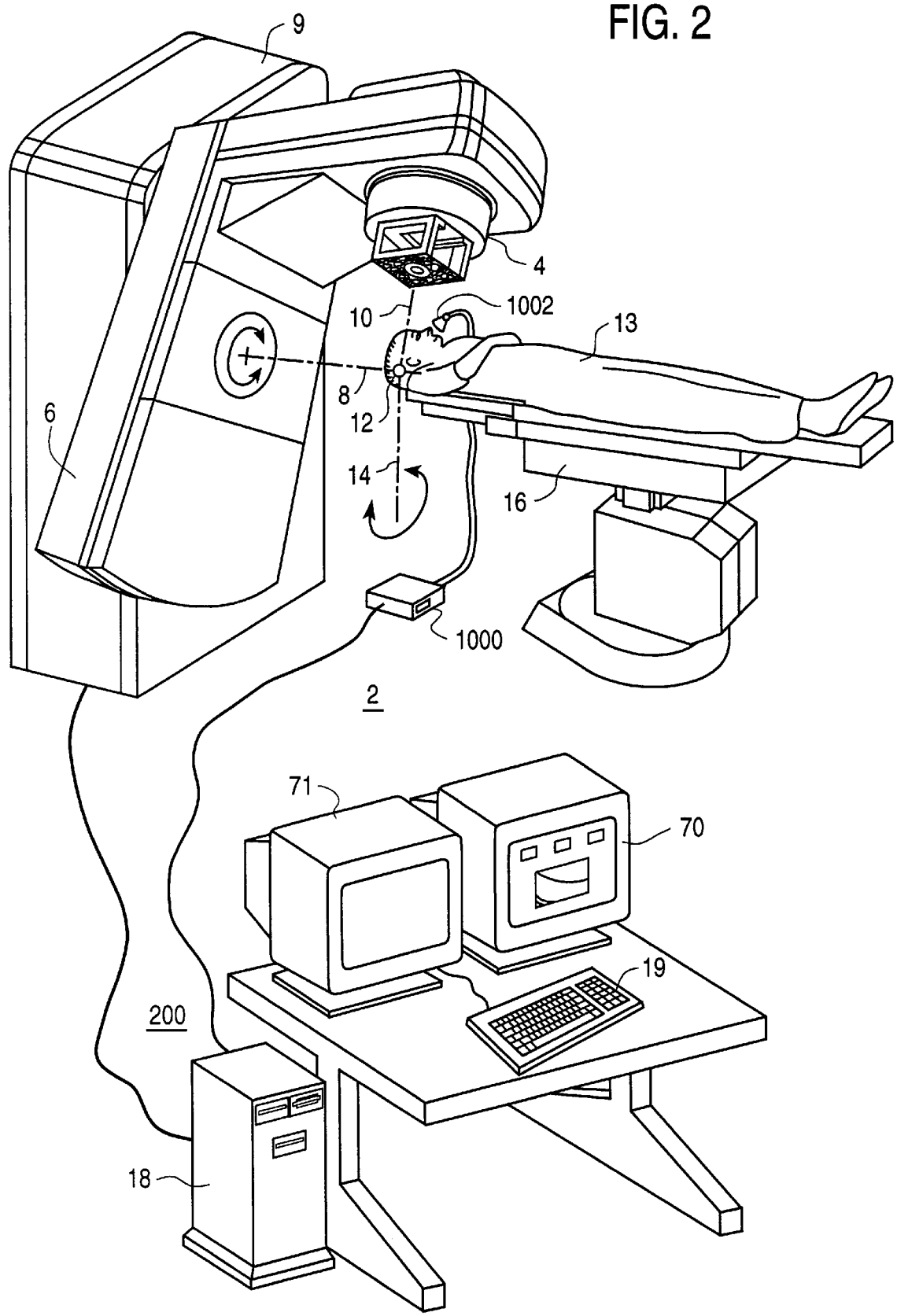
FIG. 2 is a diagram of a radiation treatment device and treatment console according to an embodiment of the present invention.

Turning now to the drawings and, with particular attention to FIG. 1, a radiation treatment apparatus embodying the present invention is shown therein and generally identified by reference numeral 2. The radiation therapy apparatus 2 may be a Mevatron or Primus linear accelerator available from Siemens Medical Systems. The radiation treatment apparatus 2 is configured to vary the synchronization of the RF modulator pulse and the injector pulse, for example, in conjunction with the physiology monitor 1000, as will be discussed in greater detail below. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to a projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes output devices such as at least one visual display unit or monitor 70 and an input device such as a keyboard 19. Data can be input also through data carriers such as data storage devices or a verification and recording or automatic setup system.

As discussed above, a physiology monitor 1000 may be provided to provide an indication of patient movement based on monitoring physiological parameters. The physiology monitor 1000 may be a known monitor configured to monitor muscle contraction, blinking, brain waves, heart movement or respiration. In particular, the physiology monitor 1000 may include a sensor 1002. The physiology monitor 1000 may be a respiratory monitor such as the $CO_2$SMO+ available from Novametrix Medical Systems, Inc., Wallingford, Conn. Such a respiratory monitor incudes a capnograph to measure $CO_2$ using an infrared sensor, and a differential pressure pneumotachometer, used to measure airway pressure and calculate both airway flow and lung volume. Readings for the four respiratory parameters ($CO_2$, flow, pressure, and volume) may be obtained 100 times per second; the data are transmitted to the treatment processing unit 200 via, for example, an RS-232 interface.

As will be discussed in greater detail below, the readings from the physiology monitor 1000 are used to control a gating signal which adjusts the phase of the injector pulse and the modulator pulse relative to one another, thereby dynamically controlling the radiation treatment.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such a data storage device. Various data can be displayed before and during the treatment on the screen of the monitor 70.

SYSTEM BLOCK DIAGRAM

Figure 3:
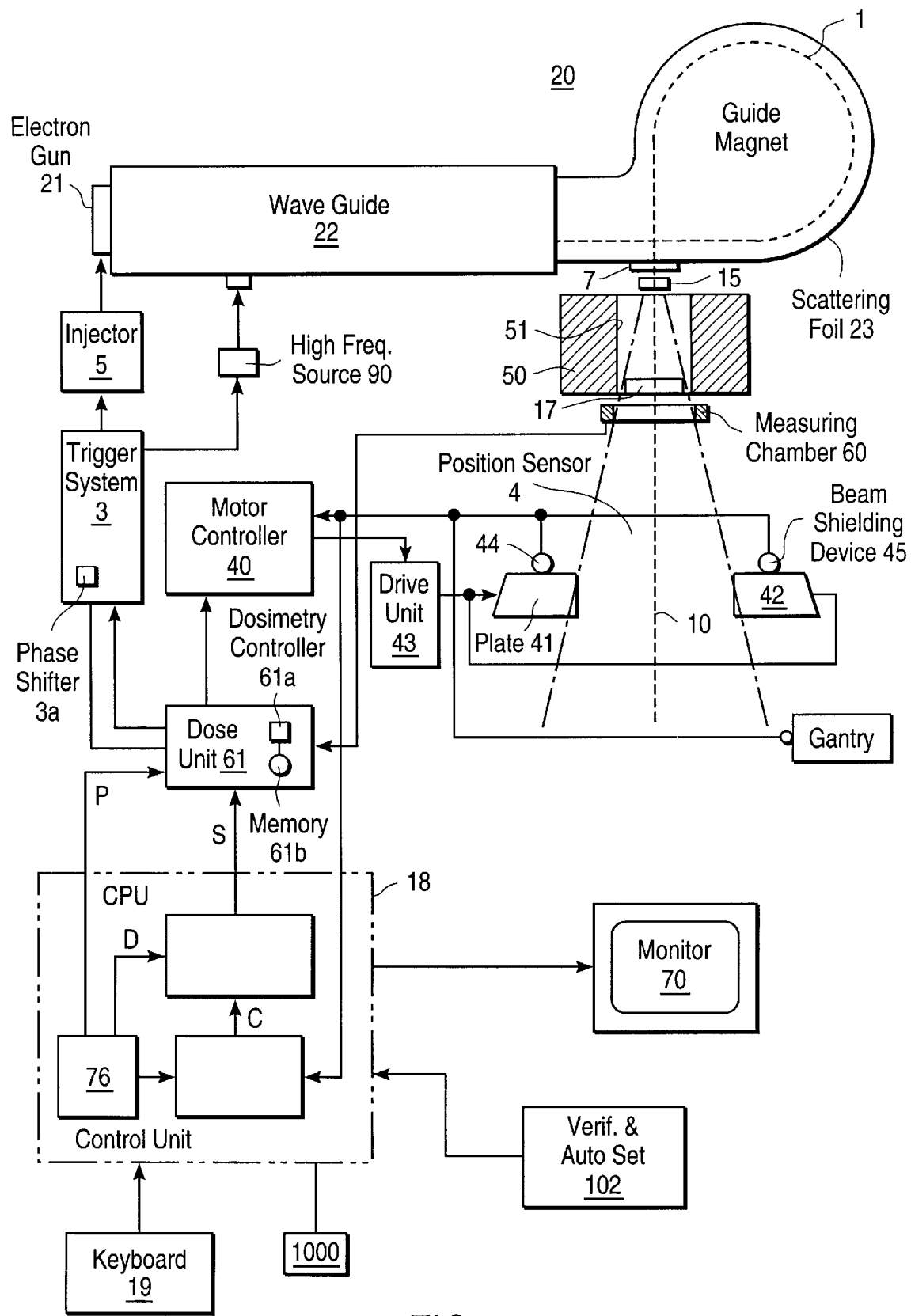
FIG. 3 is a more detailed block diagram illustrating portions of the present invention.

Turning now to FIG. 3, a block diagram of the radiation treatment device 2 and portions of the treatment unit 200 are, according to the present invention, illustrated in greater detail. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source 90, such as a magnetron or klystron, is provided, which supplies radio frequency signals for the generation of an electromagnetic field supplied to the waveguide 22. The electrons injected by the injector 5 and emitted by the electron gun 21 are accelerated by this electromagnetic field in the waveguide 22 and exit at the end opposite to electron gun 21 in electron beam 1.

As will be discussed in greater detail below, the trigger system 3 may include a phase shifter 3a for shifting the RF modulator and the injector 5 in and out of phase. In particular, the phase shifter 3a may be configured to delay the activation of the injector trigger by a predetermined period, such as 2.8 ms, to ensure that the beam is off during a pause condition. In addition, the phase shifter 3a may be configured to perform this phase shift during "gate" periods identified by the respiratory monitor 1000, as well be discussed in greater detail below.

The electron beam 1 enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 may include a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 3 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions. As discussed above, the plate arrangement 401 may alternatively or additionally include a multi-leaf collimator having many radiation blocking leaves. The leaves of such a multi-leaf collimator include a plurality of opposing leaf or rod pairs, each driven by a motor or drive unit. The drive units move the leaves in and out of the treatment field, thus creating the desired field shape. The rods, or leaves, are relatively narrow, and cast a shadow of about 0.5 to 1. cm at isocenter.

The motor controller 40 is coupled to a dose unit 61 which may include a dosimetry controller 61a according to the present invention and which is coupled to a central processing unit 18 for providing set values for the radiation beam for achieving given isodose curves. The dosimetry controller 61a according to an aspect of the present invention is configured to monitor for dose rate and accumulated dosage levels during PAUSE conditions. Accordingly, a memory unit 61b may be provided, which may store values corresponding to dose rate and accumulated dosage thresholds, as will be discussed in greater detail below. According to the present invention, if the detected dose rate and the dose exceed the thresholds, an interlock is asserted. In addition, as will be discussed in greater detail below, the dosimetry controller 61a is configured to generate an interlock if radiation is detected during gate off periods.

In addition, as will be discussed in greater detail below, the memory 61b may be used to store a look-up table of values used to compensate for dosimetric delays during a start-up period. A timer (not shown) may be provided to determine the start-up period and/or predetermined compensation times during the start-up period.

In operation, the output of the radiation beam is measured by a measuring chamber 60. In response to the deviation between the set values and the actual values, the dose control unit 61 supplies signals to a trigger system 3 which changes in a known manner the pulse repetition frequency so that the deviation between the set values and the actual values of the radiation beam output is minimized. According to an aspect of the invention, when the high voltage modulator is decoupled, the measuring chamber 60 and the dose control unit 61 are configured to remain active and detect levels of applied radiation. If the levels exceed the threshold(s), the dose control unit 61 asserts an interlock, thereby shutting down the machine. In addition, the dose control unit 61 is configured to receive a GATE OFF signal from the trigger system 3; if any radiation is detected during gate off periods, an interlock is generated.

Upon start-up, the dosimetry controller 61a monitors the output of the radiation beam via the measuring chamber 60. The dosimetry controller 61a then accesses the memory 61b which contains, for example, a lookup table of correction factors and applies the correction factors to the dose such that the signals which are applied to the trigger system minimize the predictable dose error resulting from dosimetry delays.

The central processing unit 18 is programmed by the therapist according to the instructions of the oncologist and performs an optimization so that the radiation treatment device carries out the prescribed radiation treatment. The delivery of the radiation treatment is input through a keyboard 19. The central processing unit 18 is further coupled to provide set signals to the dose control unit 61 that generates the desired values of radiation for controlling trigger system 3. The trigger system 3 then adapts the pulse radiation frequency and other parameters in a corresponding, conventional manner. The central processing unit 18 further includes a control unit 76 which controls execution of the program and the opening and closing of the collimator plates 41, 42 to deliver radiation according to a desired intensity profile.

The central processing unit 18 is configured to deliver auto-sequencing of intensity modulated treatments. One or more functional units, such as a verification and auto setup unit 102, provide inputs to the CPU 18 for controlling the radiation treatment. For example, once the verification and auto set-up unit 102 has verified system set-up, a RAD ON enable signal may be provided to the CPU 18. In response, the CPU 18 may issue a RAD ON signal to the trigger system 3 via the dose unit 61. The trigger system then provides the injector and modulator triggers to the injector and modulator, respectively, to generate the applied radiation beam.

According to the present invention, the central processing unit 18 is configured to automatically deliver predetermined sequences of treatment fields, each field in the sequence being referred to as a segment. In order to do so, the treatment beam must be cycled on and off quickly, and stray doses prevented. This capability is provided by ensuring a rapid stabilization sequence for the high voltage and RF power systems prior to BEAM ON.

PRECISION BEAM CONTROL

Figure 4:
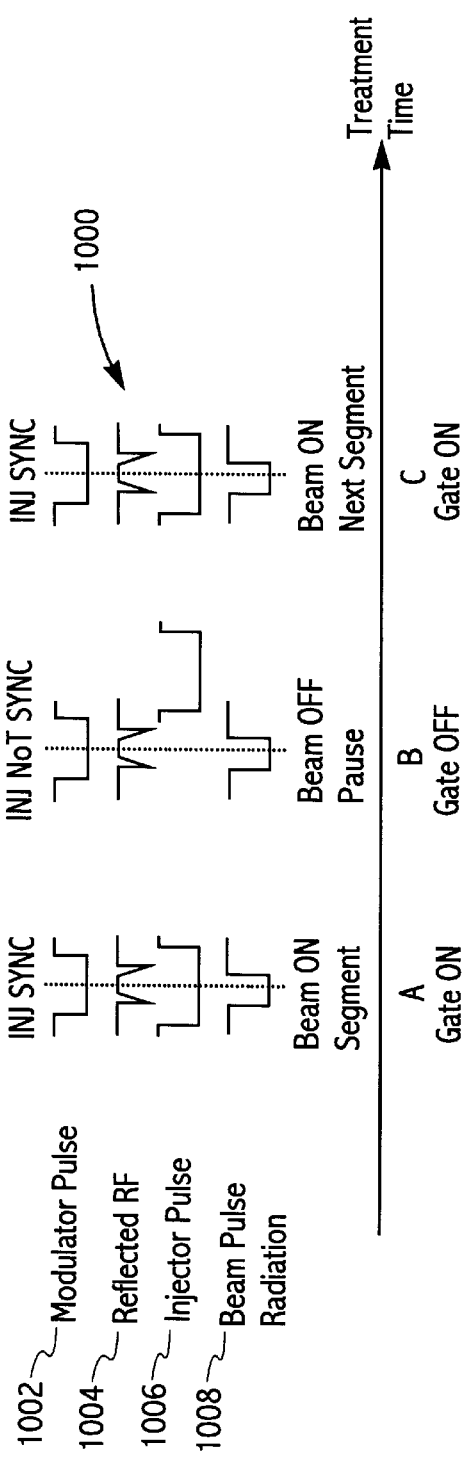
FIG. 4 is a diagram of an exemplary pulse sequence.

Turning now to FIG. 4, a diagram 1000 illustrating the techniques of the present invention is shown. In particular, sequences of RF modulator pulses 1002, reflected RF pulses 1004, injector pulses 1006, and beam pulse 1008 are illustrated. During time A, a BEAM ON segment is shown, with the injector pulse 1006 and the modulator pulse 1002 synchronized. Time A is representative of, for example, the delivery of a radiation treatment field. During time B, a BEAM OFF or pause condition is shown. Time B is the period between delivery of segments during the intensity modulated radiation treatment. During this period, various parameters of the delivery may be changed in the auto-sequence. For example, the collimator leaf positions or gantry angle may be adjusted. During time B, the injector pulse 1006 and the modulator pulse 1002 are out of synchronization, so as to ensure that radiation is not applied to the patient. To do so, a predetermined delay may be inserted into the injector pulse sequence to ensure that the injector pulse 1006 lags the modulator pulse 1002. For example, as will be discussed in greater detail below, the injector trigger may be delayed relative to the modulator trigger by 2.8 milliseconds. Finally, during time C, the BEAM ON condition is resumed for delivery of the next segment. Accordingly, the injector pulse 1006 is again synchronized with the RF modulator pulse 1002. Thus, the injector trigger delay is removed. The times A, B, C, may also represent GATE ON and GATE OFF periods, as will be discussed in greater detail below.

Figure 5:
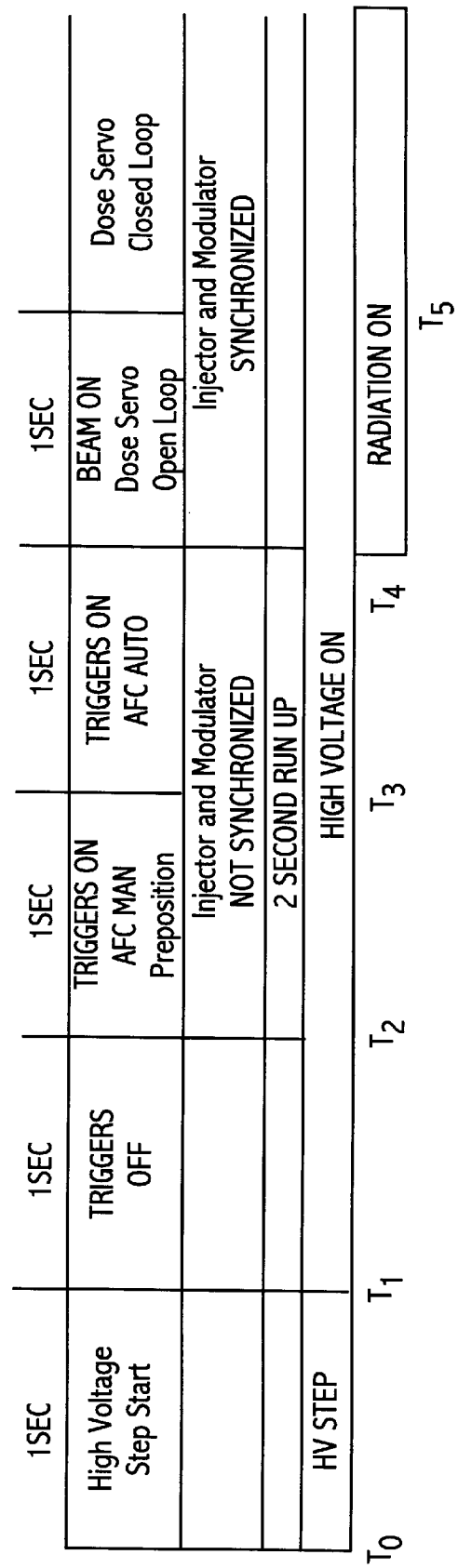
FIG. 5 is a diagram illustrating an initialization sequence according to an embodiment of the invention.

Turning now to FIG. 5, a schematic 400 of the initial stabilization sequence is illustrated. At time $T_0$, power is turned on during the high voltage step. For example, the CPU 18 may respond to a command to start or initialize the system. This initializes the high voltage system. The high voltage step start lasts until time $T_1$, for example, about 1 second. At time $T_1$, the high voltage is on. However, the CPU 18 does not activate the trigger system 3 until time $T_2$. At time $T_2$, the trigger system 3 is activated, for example, by the trigger system 3 receiving the RAD ON signal from the CPU 18. While the triggers are activated, the injector trigger is delayed relative to the modulator pulse. Thus, the injector and modulator are not synchronized. In addition, the auto frequency controls are set to manual. This allows the RF to stabilize and the AFC prepositioning to set the operating frequency within a predetermined bandwidth so that proper AFC servo operation occurs when the AFC is set to auto. At time $T_3$, the triggers are on and the auto-frequency controls are set to automatic. The injector and modulator remain unsynchronized. At time $T_4$, the RAD ON condition is set. The trigger system 3 de-activates the phase shifter 3a such that the injector trigger and the modulator trigger are delivered in synchronization with one another. Consequently, the BEAM ON condition is set, with the dose servo open loop. At time $T_5$, the dose servo is closed loop (The dose servo controls the dose rate, which is a measure of dose delivered per unit time. The dose rate is determined by magnitude of dose per pulse times the dose servo period. The dose rate is controlled by adjusting the pulse repetition frequency of the system. The open loop period allows for sufficient dose servo period to elapse before closing the servo loop). The next pause state is entered into by phase shifting the injector pulse relative to the modulator pulse.

Figure 6:
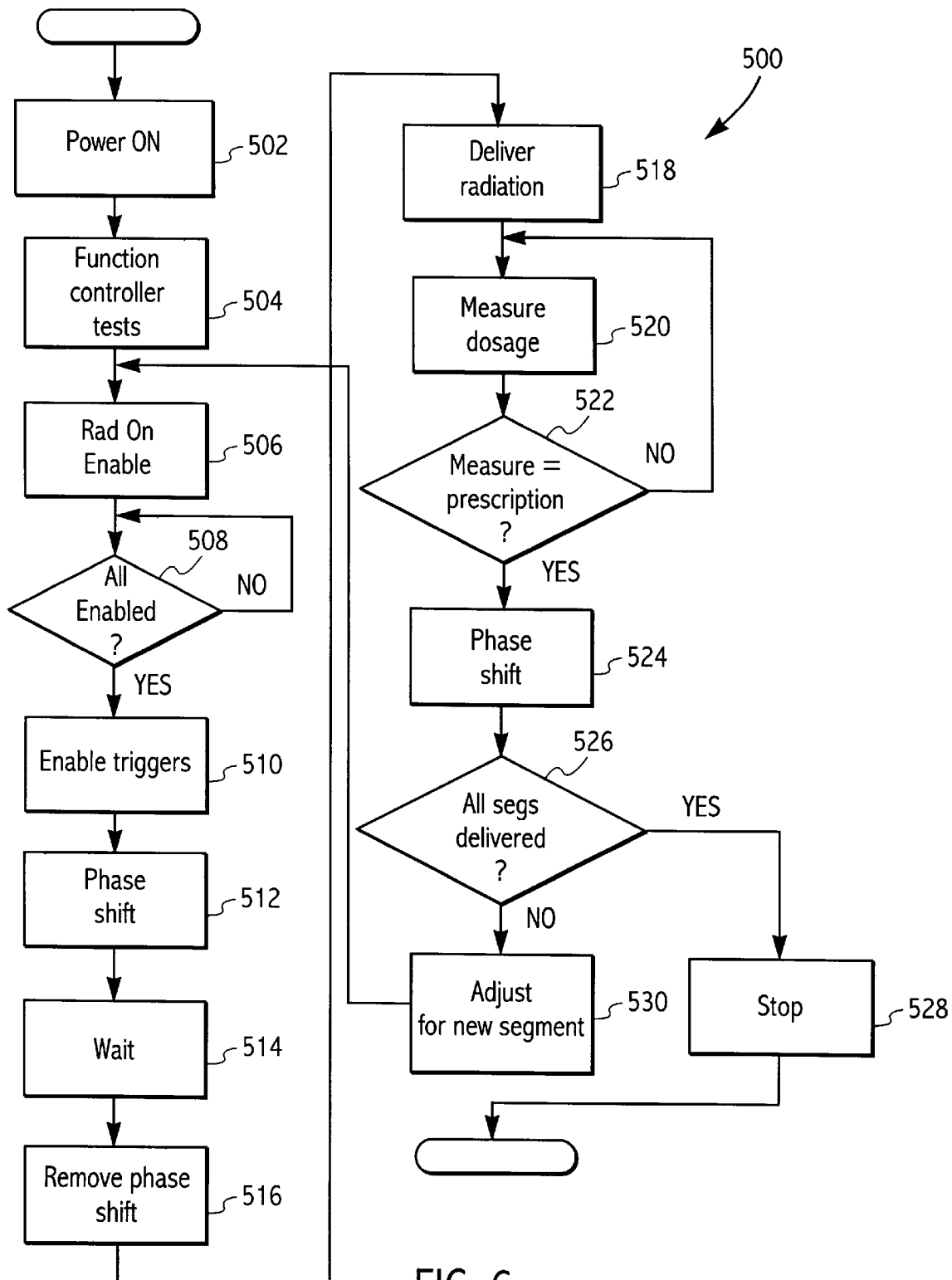
FIG. 6 is a flowchart illustrating operation of a method according to an embodiment of the invention.

Turning now to FIG. 6, a flowchart of system operation is illustrated. In a step 502, power is turned on. At this time, in a step 504, the verification and auto setup unit 102 performs a system test, ensuring, for example, that the collimator leaves are properly positioned for the particular segment. RAD ON Enable commands may be transmitted to the CPU 18 in a step 506. In a step 508, the CPU 18 determines whether all of the function controllers have provided a Rad On Enable signal. If not, the CPU 18 waits until all are received. If all the function controllers have provided a Rad On Enable signal, then the CPU 18 provides a Rad On signal to the trigger system 3, in a step 510. The trigger system 3 initiates the injector and modulator triggers in a step 512. However, the injector trigger is delayed for 2.8 ms relative to the modulator trigger by activating the phase shifter 3a. This ensures that no radiation is delivered.

After a wait period (step 514), determined for example, by an internal counter, the trigger system 3 deactivates the phase shifter 3a, in a step 516. At this time, radiation is delivered for the treatment segment in a step 518. The dose measurement unit 60 monitors the delivered dosage in a step 520. The measurement information is provided to the dose control unit 61. The dose control unit 61 compares the measured dosage to the prescribed dosage, in a step 522. The monitoring continues while the delivered dosage is less than the prescribed dosage. If the two are determined to be equal, then in a step 524, the trigger system 3 activates the phase shifter 3a, to de-synchronize the modulator and the injector, such that radiation is no longer delivered to the patient.

If all segments have been delivered, as determined in a step 526, then the CPU 18 shuts down the power in a step 528. However, if not all the segments have been delivered, then the modulator and the injector are maintained out of synchronization while the system settings are adjusted for the new segment, in a step 530.

DOSE MONITORING

As discussed above, the radiation therapy device is configured to deliver radiation according to an auto-sequence of intensity modulated field segments. Between field segments, a PAUSE state is entered. In particular, upon entering the PAUSE condition, the verification and auto set up unit 102 receives the previous segment's treatment results from the CPU 18. In addition, the verification and auto set up unit 102 downloads the next field segment to the CPU 18. When the new segment has been received, the CPU 18 automatically moves the jaws 41, 42 and multi-leaf collimator leaves (if required) as well as the gantry and treatment head, if required. In one embodiment, the high voltage may be turned off by the CPU 18 during the PAUSE state. In another embodiment, the injector pulse and the RF modulator pulse are desynchronized; but the high voltage stays on. However, no radiation is delivered.

According to the present invention, the CPU 18 monitors the dose rate and accumulated dose signals at the end of each segment. If the dose controller 61 detects that either the dose rate or the accumulated dosage exceed predetermined thresholds, then an interlock is generated and the system is shut down.

Figure 7:
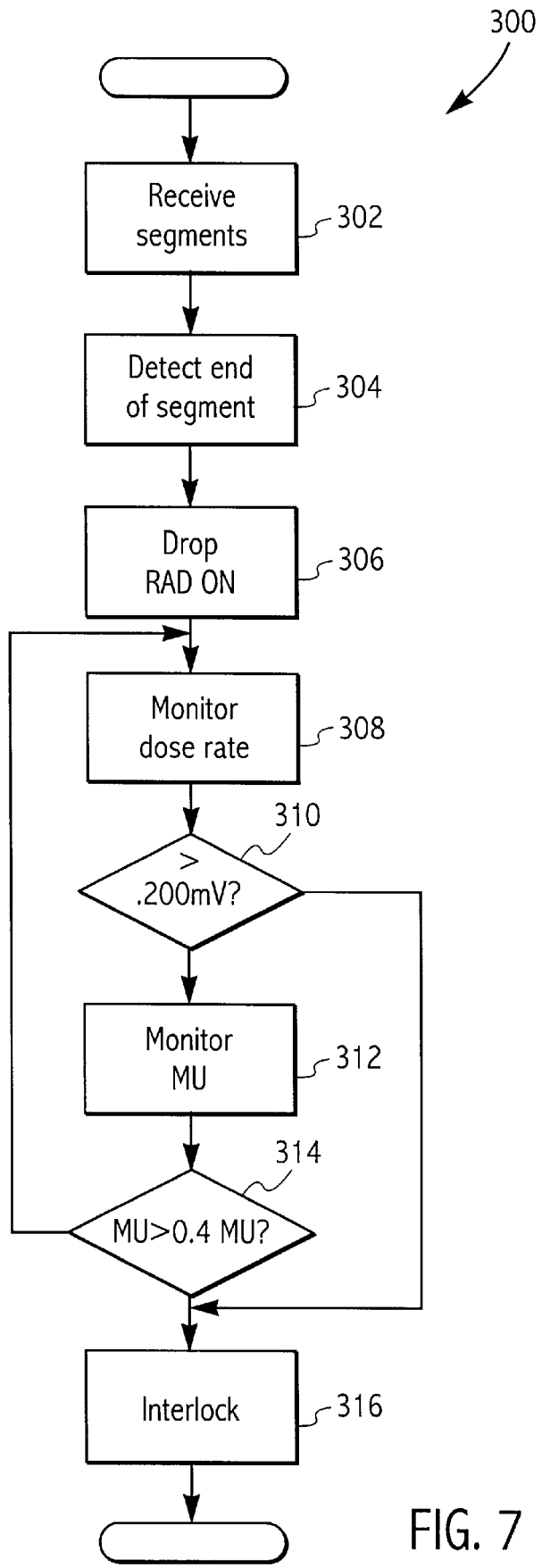
FIG. 7 is a flowchart illustrating a method for dose monitoring according to an aspect of the present invention.

Turning now to FIG. 7, a flow chart 300 illustrating operation of the embodiment of the present invention is shown. In particular, in a step 302, the CPU 18 receives the segment specifications from the verify and auto set up unit 102. Reception of the segment includes reception of an <R> command that indicates that the segment is a non-final segment. In addition, the received segment specification includes threshold values for the dosage rate and accumulated dosage which are stored by the CPU 18 in a memory unit. At the end of the non-final segment, the CPU 18 drops RAD ON but leaves HV ON (high voltage on) enabled until the start of the next segment. In one embodiment, this applies only if the subsequent segment is defined with the same energy, accessories, table position and beam shield position as in the previous segment. In a step 304, the CPU 18 detects the end of the segment. In a step 306, the CPU 18 drops RAD ON and maintains HV ON as enabled in response to the received <R>command. For a final segment, the high voltage is dropped at the completion of the treatment. In a step 308, the CPU continues to monitor the dose rate by receiving inputs from the measurement unit 60 via the dose unit 61. In particular, in one embodiment, at 30 milliseconds after the RAD ON line goes low (with the high voltage on line maintained high), if the monitored dose rate signal exceeds 200 millivolts (which is proportional to the dose rate), as determined in a step 310, then the CPU 18 asserts an interlock in a step 316. The interlock shuts down the system so that no further radiation is delivered. In addition, in one embodiment 500 milliseconds after the RAD ON line goes low (with the high voltage on line high), the number of monitor units (MU) delivered is measured in a step 312. If the number of monitor units during the PAUSE condition exceeds .4 monitor units as determined in a step 314, the CPU 18 will again generate an interlock in a step 316.

PRECISION DOSIMETRY

Figure 8:
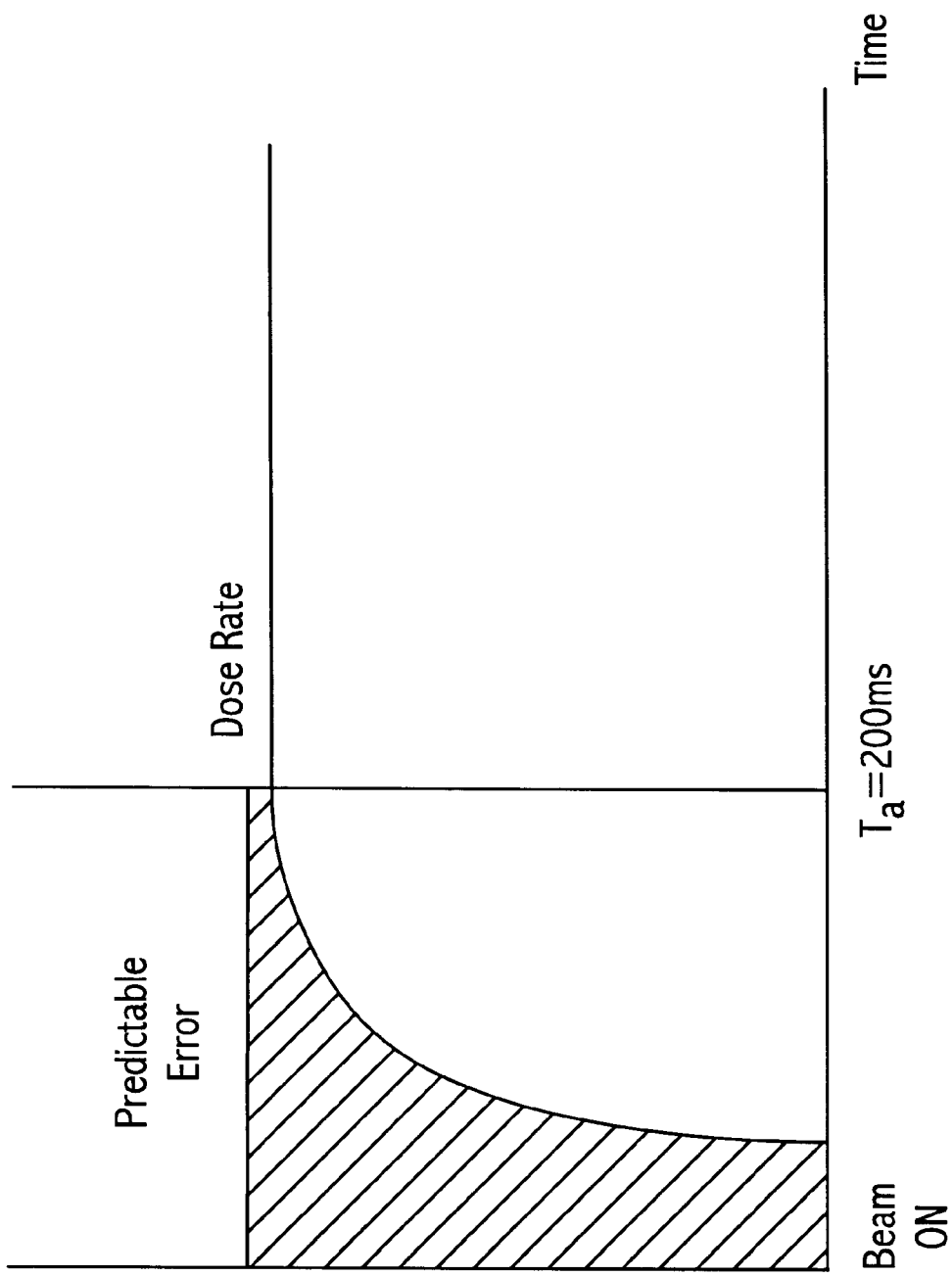
FIG. 8 is a graph of dose rate vs. time.

An important aspect of the invention relates to the initial phase of treatment, after BEAM ON. Referring now to FIG. 8, a diagram illustrating the initial phase of a beam cycle is shown. During the initial phase between BEAM ON and time $T_a$, the dose rate rises to the prescribed dose rate. In one embodiment, the time T$a$ occurs at approximately 200 milliseconds. During this time, the detected dose rate is known to lag behind the actual dose rate by a known, empirically-derived period. A radiation treatment apparatus according to the present invention compensates for this lag.

Figure 9:
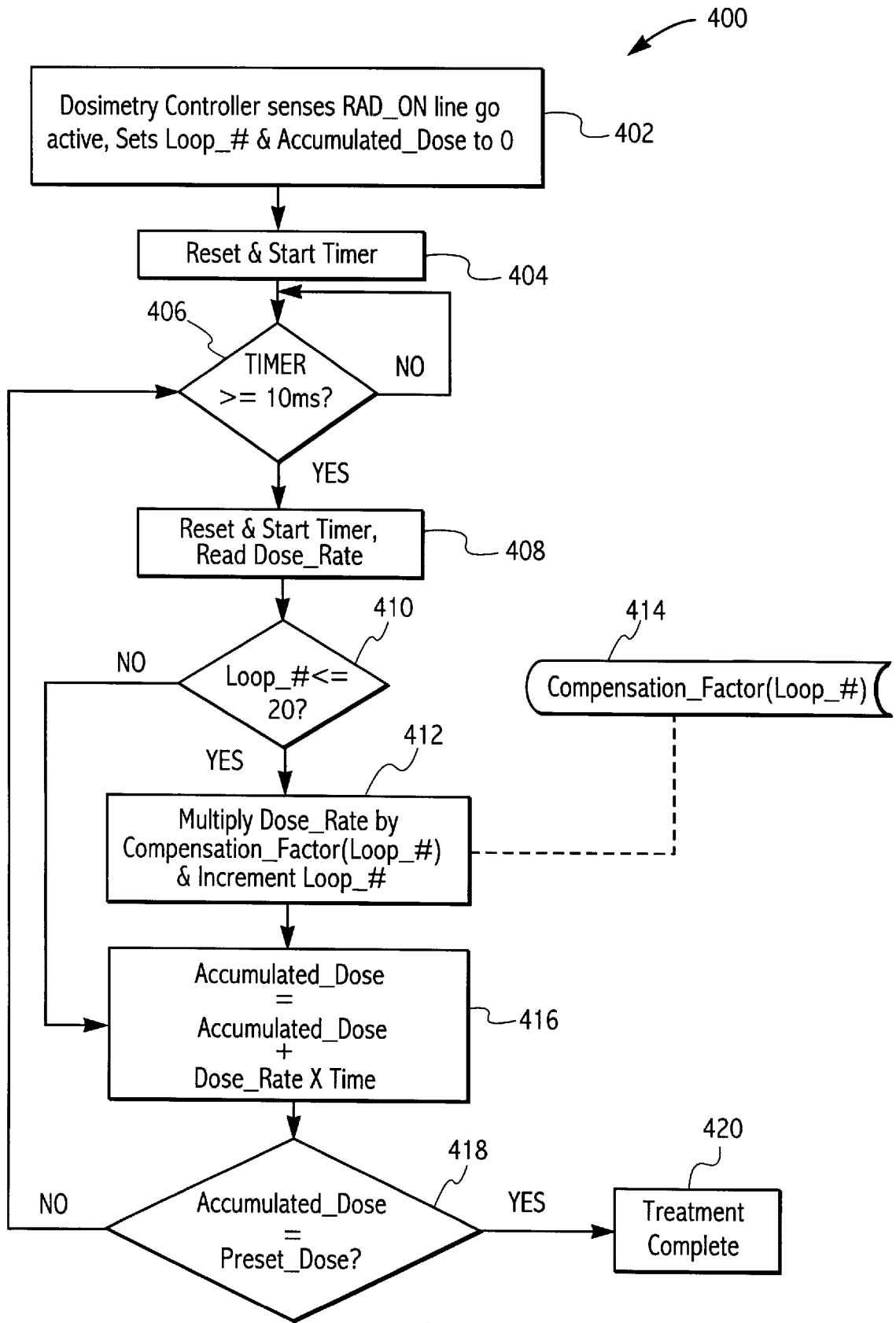
FIG. 9 is a flowchart of a method for precision dosimetry according to an aspect of the invention.

For example, FIG. 9, is a diagram illustrating the dose rate and loop number and compensation factor. In particular, the horizontal axis shows the loop number, which is representative of elapsed time, as will be discussed in greater detail below. As can be seen, the dose rate represented by a curve 902 increases from zero up to a predetermined level at a loop number equal to 20. A dose rate error occurs between loops zero and 20. Accordingly, a compensation factor, represented by the curve 904, is provided between loop 0 and 20 to overcome the delay from the dosimetry calculations.

Figure 10:
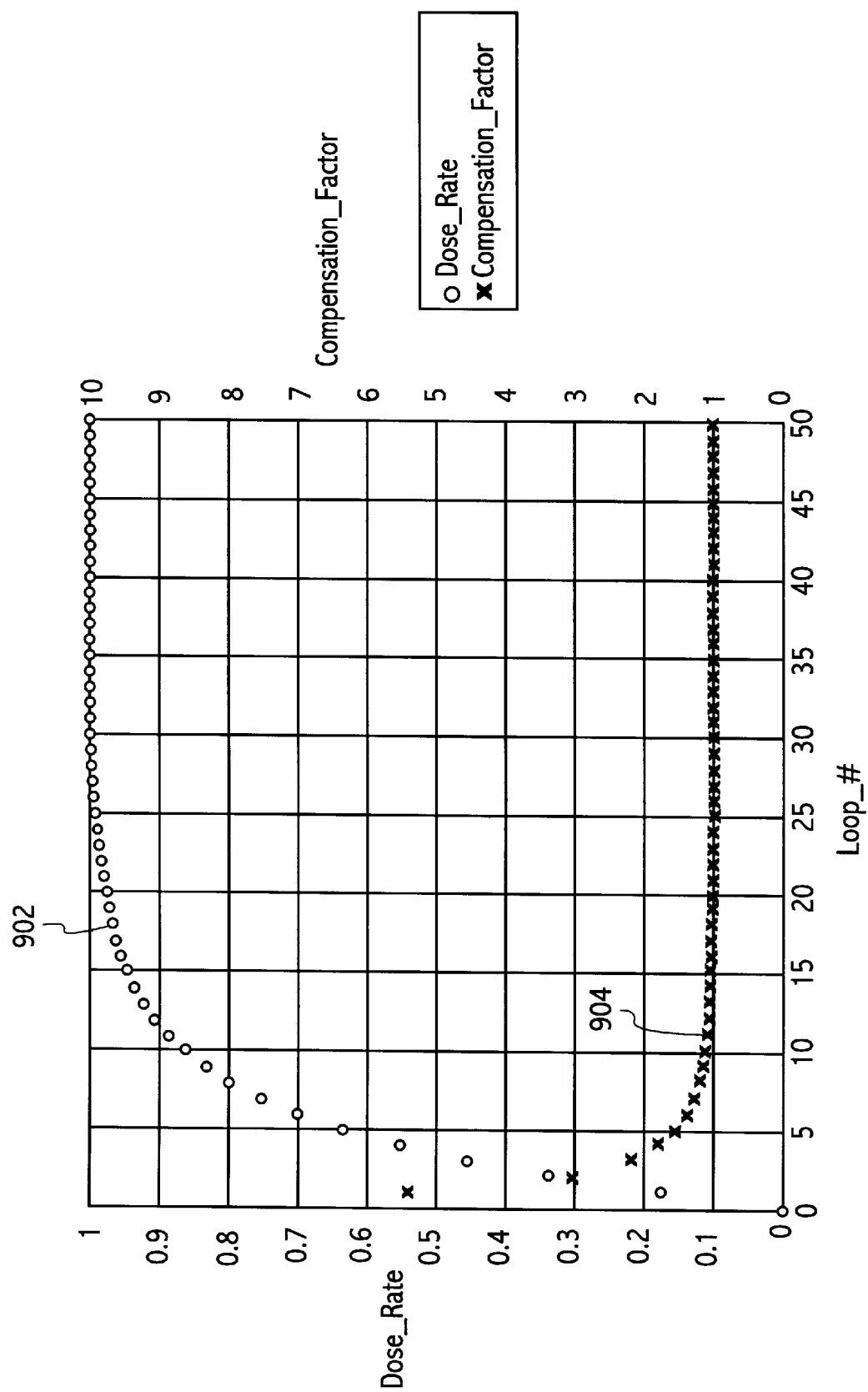
FIG. 10 is a diagram of dose rate and compensation factor vs. loop number according to the present invention.

Turning now to FIG. 10, a flowchart illustrating the correction technique according to the present invention is shown. The system samples the dosage periodically during the 200 millisecond startup period and corrects for the amplification delays. In particular, in a step 402, the dosimetry controller 61 senses the RAD ON line going active, sets a loop number and an accumulated dose variable to zero. The loop number in the embodiment illustrated is a number between 1 and 20, with the sampling occurring every ten milliseconds. It is noted that more or fewer loops may be employed. In a step 404, the dosimetry controller 61a resets and starts the timer. In a step 406, it is determined whether the timer is greater than or equal to ten milliseconds. If not, the system recycles. If the timer in step 406 was greater than or equal to ten milliseconds, then in a step 408 the timer is reset and restarted and the dose rate is read by the dosimetry controller 61a via the monitoring chamber 60.

Next, in a step 410, the dosimetry controller 61a determines whether or not the loop number is less than or equal to 20. If so, then in a step 412 the dosimetry controller will multiply the dose rate by the compensation factor which is a function of the loop number and will increment the loop number. As discussed above, the compensation factor 14 is stored in a lookup table 61b and is known through empirical system analysis. For example, dosage measurements may be made from known test systems external to the radiation therapy device. Discrepancies between the dosage determined by the external test device and the radiation treatment apparatus itself are used to establish the correction factors.

If, in step 410, the loop number was not less than or equal to 20, then in a step 416, the accumulated dose is reset to the accumulated dose's previous value plus the dose rate times time. Next, in a step 418, the system determines whether the accumulated dose is equal to the preset dose. If not, then the program cycles back to step 406. However, if the accumulated dose is now equal to the preset dose, then the treatment is completed in a step 420.

PHYSIOLOGY GATED RADIOTHERAPY

As discussed above, the present invention monitors one or more predetermined physiological parameters and BEAM ON is allowed only when the parameters are within acceptable limits. Thus, for example, referring back to FIG. 4, the periods A & C are representative of GATE ON periods and period B is representative of GATE OFF period. During period B (GATE OFF), the injector pulse 1006 and the RF modulator pulse 1002 are phase-shifted relative to one another so that the beam is off.

Figure 11:
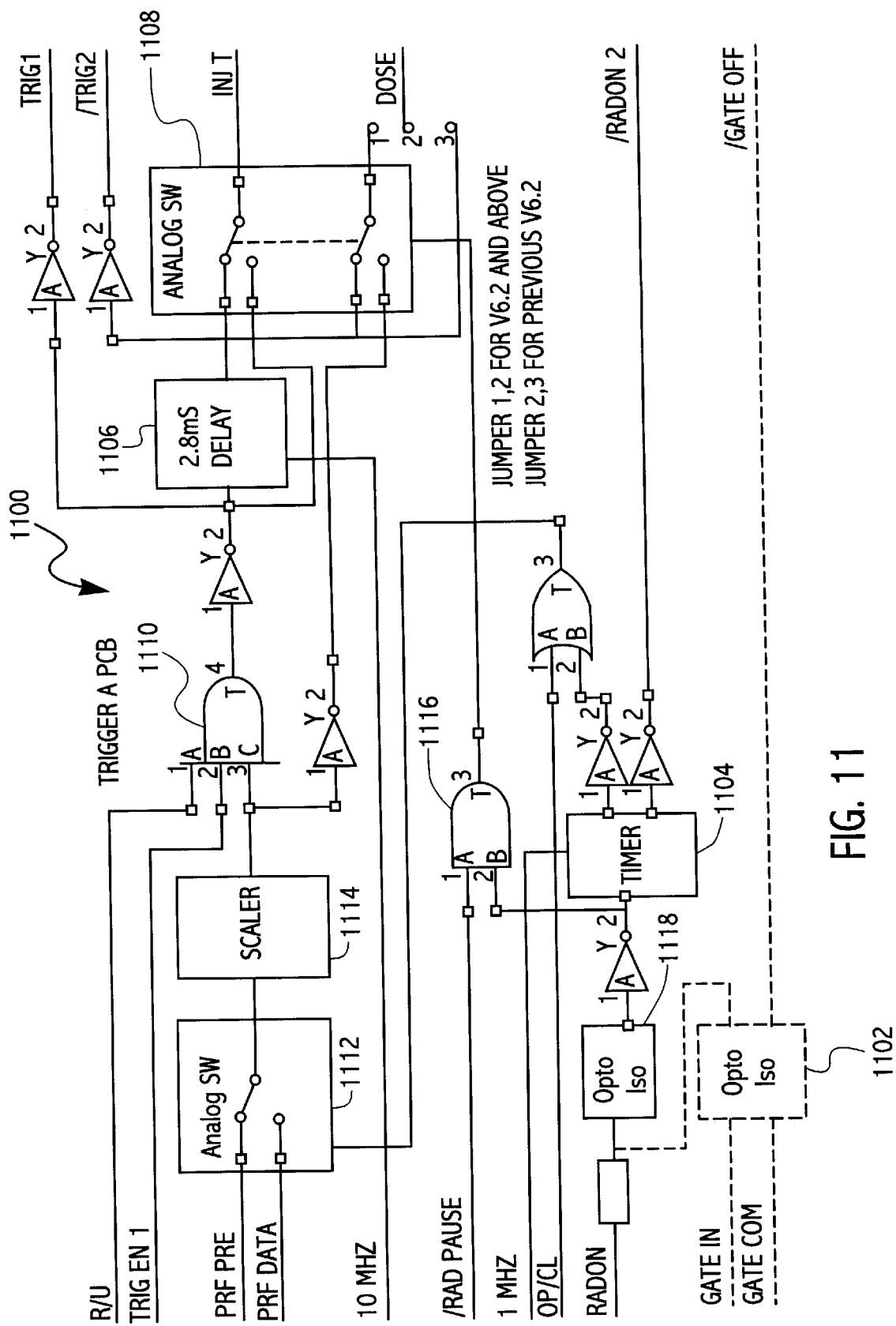
FIG. 11 is a diagram of a gating interface according to an embodiment of the invention.

Turning now to FIG. 11, an exemplary interface circuit configured for treatment gating according to the present invention is shown. In particular, the interface circuit 1100 is representative of a controller in a Primus linear accelerator available from Siemens Medical Systems, Concord, Calif. The interface circuit 1100 thus is configured to receive a plurality of inputs and to generate the trigger and injector and RAD ON pulses. Known inputs include a variety of clocks, such as a 1 megahertz clock for the timer 1104, a 10 megahertz clock for the delay circuit 1106, a RAD ON input and pulse repetition frequency (PRF) inputs, as well as trigger enable inputs. In addition, the circuit 1100 receives a GATE IN and GATE COM input into an opto-isolator 1102. The GATE COM input is simply the common ground; the GATE IN input is a signal received from an external patient physiology processor or monitor (not shown). The GATE IN signal transitions from low to high throughout the treatment with a frequency depending upon the physiological condition of the patient. As can be appreciated, the RAD ON input controls operation of a switch 1108 to provide the injector INJ control. A delay circuit 1106 is provided in the path of the TRIG EN signal; the switch 1108 switches the delay in and out of the enable path. During a gated treatment, the GATE IN signal overrides the RAD ON state and causes the injector INJ and /TRIG2 to be 2.8 milliseconds out of synchronization. According to one embodiment, a high value for GATE IN accomplishes this, although in alternate embodiments, a low value may be used. Beam generation ceases during this state and will continue when the GATE IN signal transitions to a low logic level (<N2.5V). In addition, the linear accelerator continually monitors the GATE OFF signal, which is an output from the opto isolator 1102, and monitors for applied dosages when this signal is active. If any dose is detected during this condition a known interlock terminates the treatment.

It is noted that a variety of input circuitry configured to receive signals indicative of physiological parameters may be employed, such as relays, logic gates, transistor switches, combinatorial logic, and the like. Thus, FIG. 11 is exemplary only.

In the context of respiratory gated radiotherapy, it is known that the optimal time either to acquire images or to turn the linear accelerator beam on is at the point of maximum exhalation. At this point in the respiratory cycle the diaphragm position is most reproducible and the diaphragm velocity is at a minimum.

Figure 12:
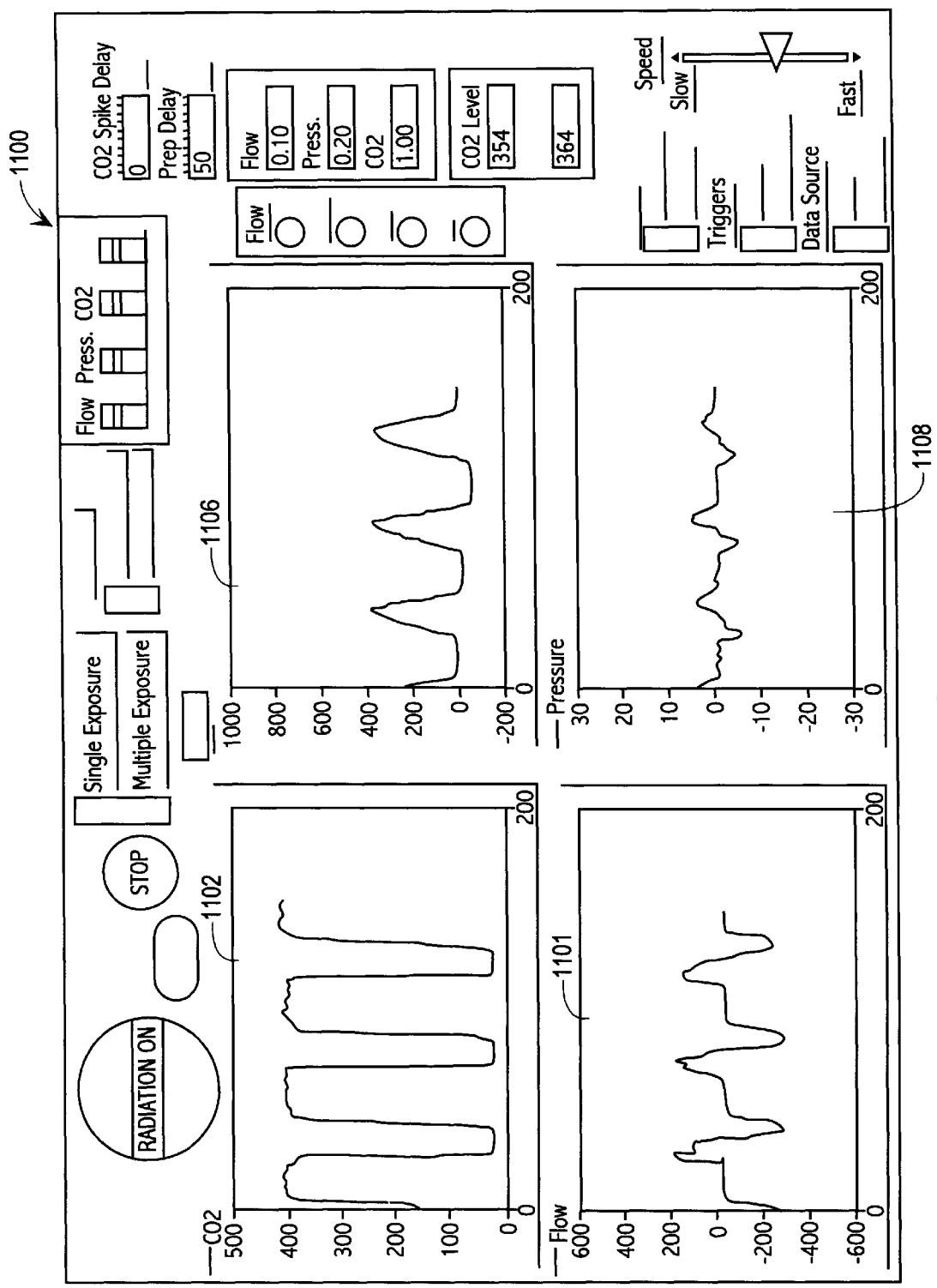
FIG. 12 is a diagram of an exemplary graphical user interface.

Turning now to FIG. 12, a graphical user interface 1100 is illustrated which shows the use of each of the respiratory parameters. Thus, the $CO_2$ is illustrated as graph 1102, the air flow is illustrated as graph 1104, the volume is illustrated as graph 1106, and the air pressure is illustrated as graph 1108. Use of the four parameters may be accomplished in different ways to gate the radiation on and off. In particular, radiation may be gated using a single exposure full exhalation (SEFE) algorithm, a single exposure full inhalation (SEFI) algorithm, a combination of SEFE and SEFI (SEFE+SEFI) a continuous exposure hold at full exhalation (CEHFE) algorithm, or a continuous exposure centered about full exhalation (CECAFE) algorithm.

The SEFE system is useful, for example, during acquisition of a single X-ray image such as a radiograph on a radiation therapy simulator. During SEFE, at the end of exhalation, air flow and pressure approach zero long volume is at a minimum and $CO_2$ level is at a maximum. At the start of inhalation, the $CO_2$ level drops sharply (i.e., $\Delta\ CO_2$ is negative), while the other parameters change more slowly from their end points. The large negative $\Delta\ CO_2$ value is used to trigger image acquisition. Insuring that the long volume is below a preset value and the $CO_2$ level is above a preset value, ensures that triggering doesn't occur at the wrong point in the respiratory cycle, such as might occur when a patient inhales after having not fully exhaled. Triggering is allowed only when the separate and redundant analysis of all four respiratory parameters indicates it is appropriate. This minimizes false positives with only a small increase in false negatives. Each of the parameters thresholds may be set interactively before image acquisition by obtaining a set of training data while the patient breathes normally.

It is often desirable to document the full range of organ motion, for example, when designing blocks for those cases in which the gated linear accelerator treatments are not being used. This requires a second exposure at the point of full inhalation in addition to the one obtained at full exhalation. At full inhalation, air flow and pressure again approach zero but $CO_2$, $\Delta\ CO_2$ and long volume values are reversed from full exhalation. Thus, with the SEFI triggering occurs when $\Delta\ CO_2$ becomes sharply positive. The point of full inhalation is not as reproducible as full exhalation, but careful setting of the $CO_2$ and long volume limits ensure exposure at the proper point. A doubly exposed radiograph documenting the two extreme diaphragm positions can be obtained by using a double exposure algorithm which is a combination of the two single exposure algorithms described above.

The CEHFE algorithm is used to obtained images continuously with the diaphragm in a fixed reproducible position. Patients are instructed to hold their breath for short periods of time, typically two to three seconds after exhalation. Image acquisition commences when respiratory parameters are similar to those used by the SEFE algorithm except for the $\Delta\ CO_2$ which is now equal to zero. At the instant the patient begins inhaling, $\Delta\ CO_2$ becomes sharply negative and image acquisition terminates. Images are obtained for 30 to 90 seconds, reduction of organ motion is documented radiographically and corresponds to the motion that will be obtained when the same gating algorithm is used to gate the linear accelerator.

Table 1 illustrates exemplary parameters for the CEHFE algorithm.

| PARAMETER | VALUE |
|---|---|
| $CO_2$ Derivative $\partial CO_2$ | 1.00 |
| Air Flow | 10% of Previous Maximum, |
| Air Pressure | 20% of Previous Maximum (NOT USED) |
| Lung Volume | 364 ml: Absolute Drop from Previous Maximum (Value Set Graphically) |
| $CO_2$ | 35.4 mm Hg: Absolute Level (Value Set Graphically) |

Figure 13:
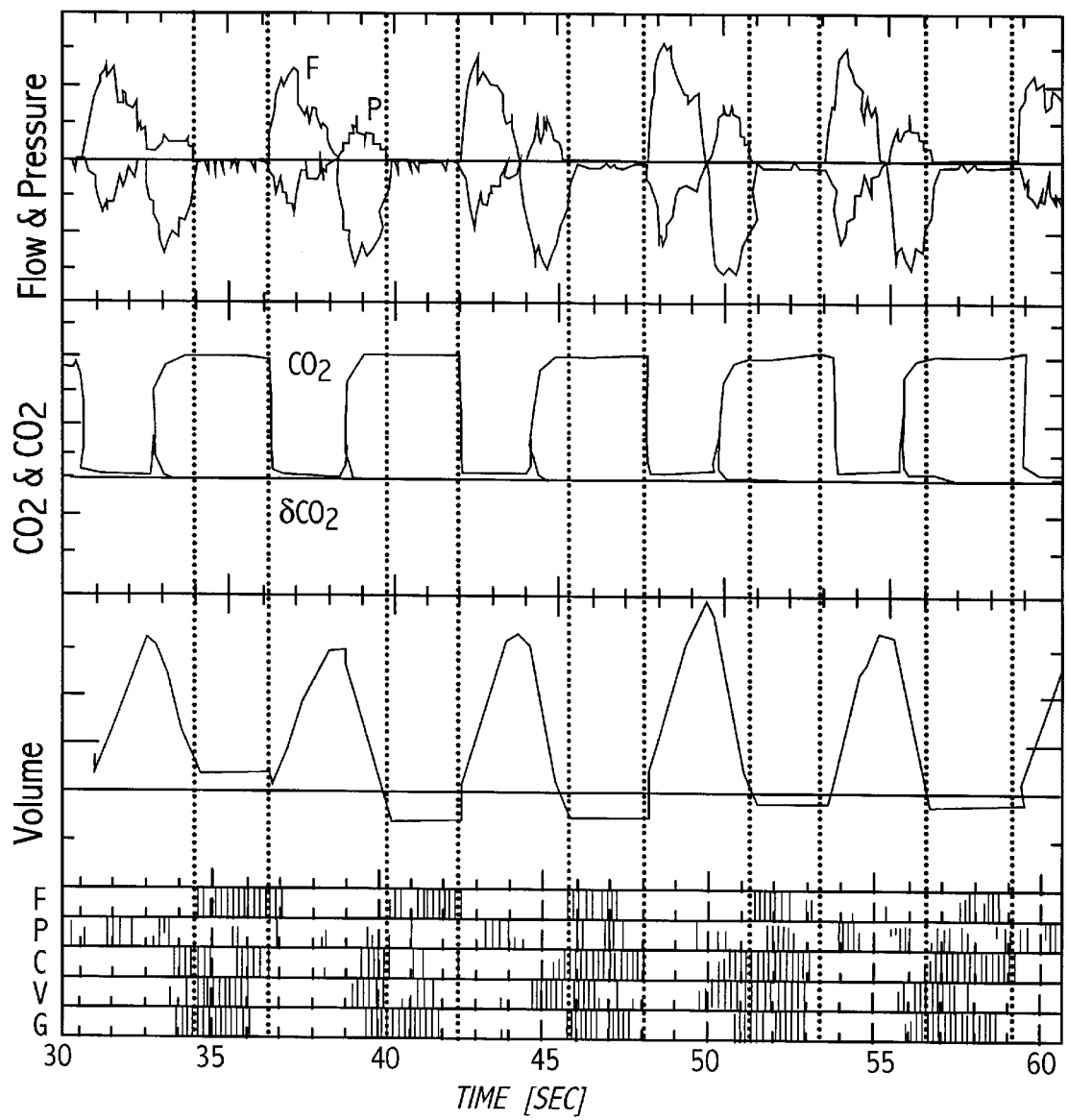
FIG. 13 is a diagram illustrating CEHFE gating.

For example, FIG. 13 illustrates a 30-second respiratory sample of the CEHFE gating algorithm for a 14-year old female with Hodgkin's disease. The shaded areas across from the "G" indicate those intervals when BEAM ON conditions are met. During "G", the gating signal G is sent to and received by the interface 1100. The figure shows gating when flow (F), $CO_2$ (C) and Volume (V) parameters are met; pressure (P) was not used and was latched 'ON'.

It is noted that due to age or medical status a limited number of patients are unable to hold their breath. In this case, the CECAFE algorithm is used. Image acquisition begins earlier in the respiratory cycle for the CEHFE algorithm by setting the threshold for acceptable long volume higher and acceptable $CO_2$ level lower. Image acquisition is allowed to continue beyond the point that $\Delta\ CO_2$ turns sharply negative for a fixed period of time, usually 2.5 seconds.

Generally, gating on the linear accelerator is accomplished using either continuous exposure algorithm with the hold breath method resulting in less diaphragm motion requiring a smaller PTV. Prior to treatment each day, a set of training data are obtained with the patient breathing normally allowing adjustment of the parameter levels used in the gating algorithm. Treatment commences with the accelerator fully powered up but with X-ray production inhibited by injecting electrons into the accelerator waveguide out of phase. Port films are obtained using the SEFE algorithm. Longer exposures, as may be required with electron and portal imaging are accomplished using one of the continuous exposure algorithms.

What is claimed is:

1. A controller for a radiation therapy apparatus comprising:
   an interface configured to receive one or more inputs indicative of a state of one or more of a patient's physiological parameters; and
   a gating controller, said gating controller configured to vary a phase between an RF pulse and an injector pulse responsive to said one or more inputs.

2. A controller according to claim 1, wherein said one or more inputs includes one or more inputs responsive to a heart monitor.

3. A controller according to claim 1, wherein said one or more inputs includes one or more inputs responsive to a muscle monitor.

4. A controller according to claim 1, wherein said one or more inputs includes one or more inputs responsive to a respiratory monitor.

5. A controller according to claim 1, wherein said one or more inputs includes one or more inputs responsive to a brain wave monitor.

6. A method for delivering radiation therapy, comprising:
   receiving one or more signals indicating that a state of one or more of a patient's physiological parameters have matched one or more predetermined criteria; and varying a phase between an RF pulse and an injector pulse responsive to said receiving.

7. A method according to claim 6, wherein said state includes a state of a heart parameter.

8. A method according to claim 6, wherein said state includes a state of a muscle parameter.

9. A method according to claim 6, wherein said state includes a state of a respiratory parameter.

10. A method according to claim 6, wherein said state includes a state of a brain parameter.

11. A radiation therapy apparatus, comprising:

means for delivering a radiation dose to a patient; and a controller for receiving an input signal indicative of one or more of said patient's physiological parameters, said controller configured to dynamically vary application of said dose responsive to said input, said controller configured to vary a phase between an RF pulse and an injector pulse responsive to said one or more inputs.

12. A radiation therapy apparatus according to claim 11, said controller configured to execute an interlock responsive to detection of a dose during a period when said RF pulse and said injector pulse are out of phase.

13. A radiation therapy apparatus according to claim 11, said input signal indicative of a respiratory parameter.

14. A radiation therapy apparatus according to claim 11, said input signal indicative of a heart parameter.

15. A radiation therapy system, comprising:

an apparatus for delivering a predetermined radiation dose to a patient;

an interface configured to receive one or more input signals indicative of one or more of said patient's physiological parameters; and a controller configured to vary a phase between an RF pulse and an injector pulse, whereby substantially no radiation is delivered to said patient when said RF pulse and said injector pulse are out of phase, and wherein said phase is varied responsive to said one or more signals indicative of one or more of said patient's physiological parameters.

16. A radiation therapy system according to claim 15, wherein said controller is configured to vary said phase by inserting a predetermined delay between said RF pulse and said injector pulse.

17. A radiation therapy system according to claim 15, said interface including an opto-isolator for receiving said one or more inputs.

18. A radiation therapy system according to claim 15, said controller configured to generate an interlock if more than a predetermined level of radiation is detected during a period when said RF pulse and said injector pulse are out of phase.

19. A radiation therapy system according to claim 15, said one or more inputs indicative of a respiratory parameter.

* * * * *